United States Patent [19]

Wang et al.

[11] Patent Number: 5,702,431
[45] Date of Patent: Dec. 30, 1997

[54] ENHANCED TRANSCUTANEOUS RECHARGING SYSTEM FOR BATTERY POWERED IMPLANTABLE MEDICAL DEVICE

[75] Inventors: Xintao Wang, Houston, Tex.; Jennifer L. Hay, Knoxville, Tenn.

[73] Assignee: Sulzer Intermedics Inc., Angleton, Tex.

[21] Appl. No.: 710,449

[22] Filed: Sep. 17, 1996

Related U.S. Application Data

[63] Continuation-in-part of Ser. No. 482,786, Jun. 7, 1995.

[51] Int. Cl.[6] .................................................. A61N 1/02
[52] U.S. Cl. ........................................... 607/61; 607/33
[58] Field of Search .................................. 607/61, 33, 31, 607/28; 320/2, 21, 39

[56] References Cited

U.S. PATENT DOCUMENTS

| | | | |
|---|---|---|---|
| 3,195,540 | 7/1965 | Waller | 128/422 |
| 3,454,012 | 7/1969 | Raddi | 128/422 |
| 3,775,661 | 11/1973 | Frezzolini et al. | 320/46 |
| 3,824,129 | 7/1974 | Fagan, Jr. | 136/6 |
| 3,865,101 | 2/1975 | Saper et al. | 128/206 |
| 3,867,950 | 2/1975 | Fischell | 128/419 |
| 3,888,260 | 6/1975 | Fischell | 128/419 |
| 3,942,535 | 3/1976 | Schulman | 128/419 |
| 4,014,346 | 3/1977 | Brownlee et al. | 128/419 |
| 4,057,069 | 11/1977 | Dorffer et al. | 128/421 |
| 4,082,097 | 4/1978 | Mann et al. | 128/419 |
| 4,096,856 | 6/1978 | Smith et al. | 128/419 |
| 4,096,866 | 6/1978 | Fischell | 128/419 |
| 4,134,408 | 1/1979 | Brownlee et al. | 128/419 |
| 4,172,459 | 10/1979 | Hepp | 128/697 |
| 4,275,739 | 6/1981 | Fischell | 128/419 |
| 4,323,075 | 4/1982 | Langer | 128/419 |
| 4,409,647 | 10/1983 | Terkanian | 363/27 |
| 4,432,363 | 2/1984 | Kakegawa | 128/419 |
| 4,548,209 | 10/1985 | Wielders et al. | 128/419 |
| 4,572,191 | 2/1986 | Mirowski et al. | 128/419 |
| 4,635,639 | 1/1987 | Hakala et al. | 128/419 |
| 4,661,107 | 4/1987 | Fink | 623/2 |
| 4,665,896 | 5/1987 | La Forge et al. | 128/1 |
| 4,677,534 | 6/1987 | Okochi | 363/21 |
| 4,787,389 | 11/1988 | Tarjan | 128/419 |
| 4,827,936 | 5/1989 | Pless et al. | 128/419 |
| 4,903,699 | 2/1990 | Baker, Jr. et al. | 128/419 |
| 5,184,059 | 2/1993 | Patino et al. | 320/39 |
| 5,279,292 | 1/1994 | Baumann et al. | 607/137 |
| 5,285,779 | 2/1994 | Cameron et al. | 607/5 |
| 5,314,453 | 5/1994 | Jeutter | 607/61 |
| 5,350,413 | 9/1994 | Miller | 607/61 |
| 5,411,537 | 5/1995 | Munshi et al. | 607/33 |

OTHER PUBLICATIONS

Sipex Corporation Signal Processing Excellence; Analog Array ASIC Design Manual, Mar. 1991 (Chapter 3).

*Primary Examiner*—Scott M. Getzow
*Attorney, Agent, or Firm*—John R. Merkling

[57] ABSTRACT

An improved transcutaneous energy transmission device is disclosed for charging rechargeable batteries in an implanted medical device and to minimize peak temperature rises in the implanted device. A current with a sinusoidal waveform is applied to a resonant circuit comprising a primary coil and a capacitor. Current is induced in a secondary coil attached to the implanted medical device. Two solid state switches are used to generate the sinusoidal waveform by alternately switching on and off input voltage to the resonant circuit. The present invention charges the batteries using a charging protocol that either reduces instantaneous charging current or duty cycle of a fixed charging current as the charge level in the battery increases. Peak temperature rises are less while delivering comparable electrical charge of the battery than for prior charging systems. A controller preferably is constructed as a pulse width modulation device with enable and reference voltage features to effectuate variable duty cycle control of the current level applied to the primary coil. An alignment indicator also is provided to insure proper alignment between the energy transmission device and the implanted medical device. The implantable device maximizes transcutaneous energy transmission at different current levels by placing different capacitors into the circuit depending on the magnitude of charging current. Peak temperature rises are reduced while delivering comparable electrical energy charge to the battery than for prior charging systems.

5 Claims, 8 Drawing Sheets

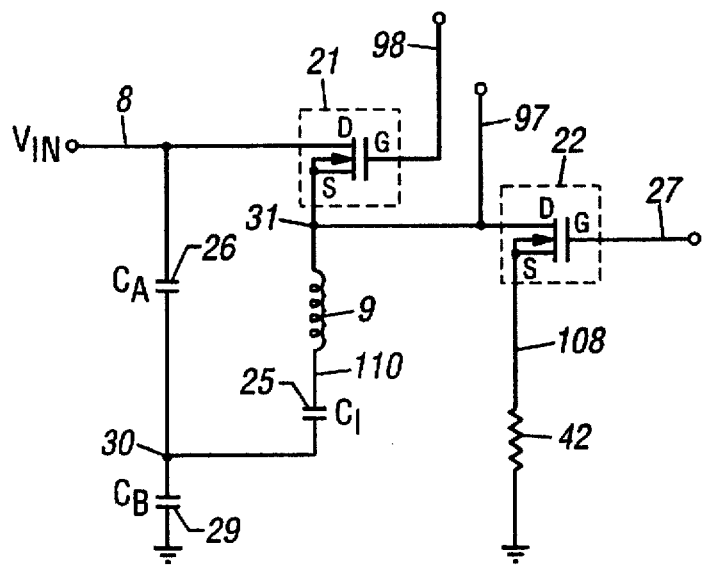
FIG. 8
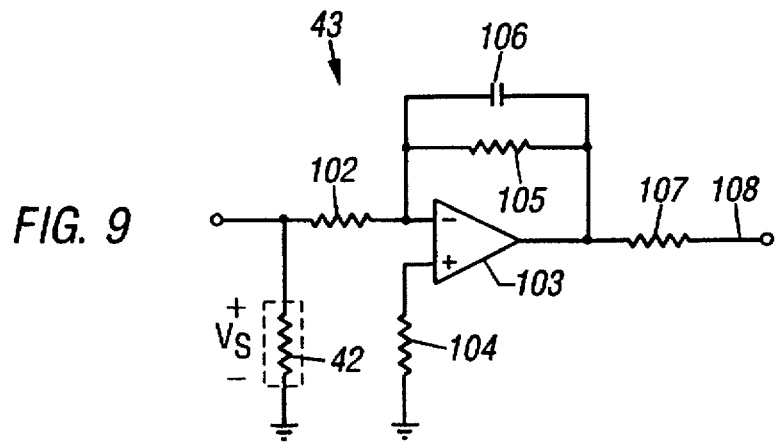
FIG. 9
FIG. 10
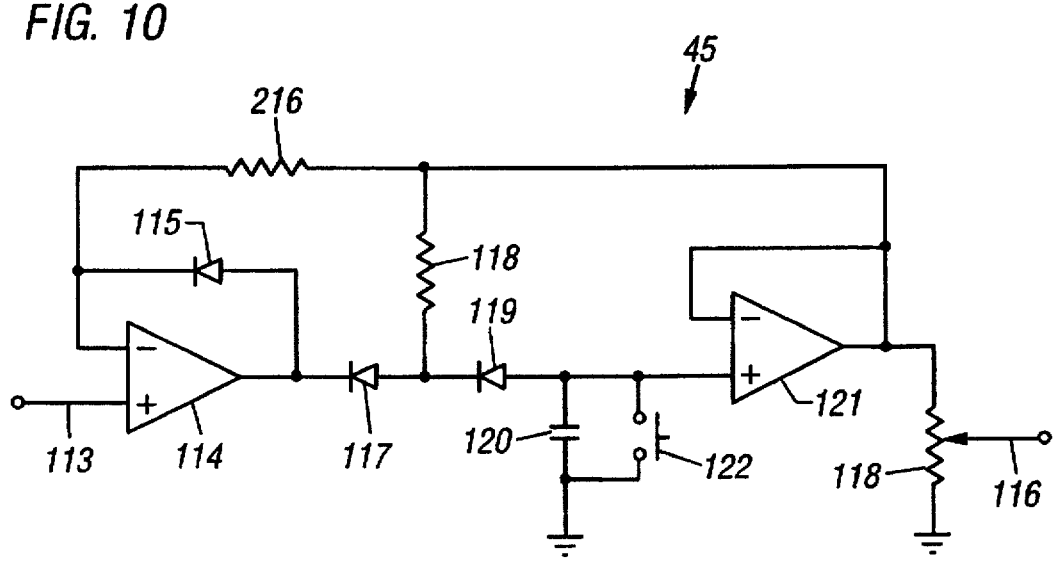

ENHANCED TRANSCUTANEOUS RECHARGING SYSTEM FOR BATTERY POWERED IMPLANTABLE MEDICAL DEVICE

CROSS REFERENCE TO RELATED APPLICATION

This is a continuation-in-part application of U.S. patent application Ser. No. 08/482,786, filed Jun. 7, 1995 entitled "Transcutaneous Energy Transmission Circuit for Implantable Medical Device," assigned to the assignee of the present invention.

BACKGROUND OF THE INVENTION

1. Field of the Invention

The present invention relates generally to a power source for an implantable medical device. More particularly, the present invention relates to an external energy transmission device for recharging batteries inside an implantable medical device. Still more particularly, the present invention relates to a charging device for remotely recharging a battery in an implanted medical device. The battery may be of the type disclosed in commonly assigned U.S. Pat. No. 5,411,537, issued May 2, 1995, entitled "Rechargeable Biomedical Battery Powered Devices With Recharging and Control System Therefor," the teachings of which are incorporated by reference herein.

2. Scope of the Relevant Art

Currently, battery operable implantable medical devices principally comprise cardiac pacemakers, but also may include heart assist systems, drug infusion and dispensing systems, defibrillators, nerve and bone growth stimulators, organ stimulators, pain suppressers and implanted sensors, to name a few. The basic cardiac pacemaker generally comprises an electrode, in contact with the heart, that connects by a flexible lead to a pulse generator. The pulse generator includes a microelectronics package, which implements the pacemaker functions, and a power source for supplying operating power to the microelectronics package and other peripheral devices and components. A "fixed rate" pacemaker continuously provides timed pulses to the heart, irrespective of proper beating, while a demand inhibited pacemaker provides pulses only when the heart fails to deliver a natural pulse. Depending upon the various sensed events, the pacemaker stimulates the right atrium, the right ventricle, or both chambers of the heart in succession. The pacemakers in current use incorporate circuits and antennae to communicate noninvasively with external programming transceivers. Most pacemakers currently used are of the demand inhibited type, and are programmable.

Early pacemakers and defibrillators typically were powered by disposable primary zinc-mercuric oxide cells. Although the popularity of this power system persisted for many years, the system suffered from high self-discharge and hydrogen gas evolution. Several mechanisms contributed to battery failure, most of which were related to cell chemistry. In addition, the open-circuit voltage of each cell was only 1.5V, with several cells connected in series to obtain the voltage required for pacing. Furthermore, because of gas evolution, these prior art pacemaker could not be hermetically sealed, and had to be encapsulated in heavy epoxy. In 1970, the average life of the pulse generator was only about two years, and about 80 percent of explants were necessitated by battery failure.

Because of such limitations, many other power generation and power storage devices have been considered as possible alternates. Research and development efforts have focused primarily on chemical batteries, nuclear batteries, and rechargeable batteries. Additional developmental efforts were directed at dividing the pacing system into two packages, with a power pack located outside the patient's body for transmitting electrical signals through wires to a passive receiver implanted in the body. Cardiac pacemakers based on rechargeable nickel-cadmium and zinc-mercuric systems also were developed. Examples of such devices are disclosed in U.S. Pat. Nos. 3,454,012; 3,824,129; 3,867,950; and 4,014,346. These rechargeable pacemakers incorporated a charging circuit which typically was energized by electromagnetic induction from a device external to the body. The electromagnetic induction produced a current in the pacemaker's charging circuit which was converted to a direct current (DC) voltage for charging the battery. Although this system was incorporated in many cardiac pacemakers, it was unpopular among patients and physicians because frequent recharging was usually necessary (sometimes on a weekly basis), and because the nickel-cadmium system suffered from memory effects which reduced the battery capacity exponentially after each recharge. In addition, the specific energy density of both types of rechargeable batteries was poor, cell voltage was low, the state-of-charge condition was difficult to ascertain, and hydrogen gas liberated during overcharge was not properly scavenged either through a recombination reaction, or hydrogen getters.

Charging nickel-cadmium cells and zinc-mercuric oxide cells is problematic. Cells of these types have a relatively flat voltage versus time curve during the charging process. The flat slope of the voltage time curve during charging provides little resolution to ascertain accurately the instantaneous percentage of full charge. Accordingly, these cells (especially nickel-cadmium), provide a poor indication of the charge level. Additionally, overcharged nickelcadmium cells liberate oxygen exothermically at the nickel which migrates to the cadmium electrode and recombines to form cadmium hydroxide. In some situations, particularly during an overcharge condition, the rate of oxygen evolution is higher than the rate of oxygen recombination. This may lead to an excessive internal pressure, forcing the cell to vent the excess gas. The overcharge reaction also heats the cell which in turn lowers cell voltage. Therefore, charging is terminated when the battery voltage begins to decrease, thus indicating the beginning of an overcharge condition.

Other techniques for controlling the charging operation have been employed. For example, U.S. Pat. No. 3,775,661 teaches that the pressure build-up internally can be sensed by a diaphragm that is external to the battery. As the pressure within the cell casing increases, the diaphragm is flexed to actuate an associated mechanical switch located in the battery charging circuit. The closure of the switch deenergizes the charger when the battery internal pressure indicates a fully charged state.

In somewhat similar fashion, U.S. Pat. No. 4,275,739 employs a diaphragm internal to the cell. Deflection of the diaphragm during an episode of increasing internal pressure indicates the cell has reached a full charge. Other examples of systems which control charge operation are U.S. Pat. Nos. 3,824,129; 3,888,260; 3,942,535; and 4,082,097.

Today, systems employing nickel-cadmium cells control battery charging use a variety of different charging techniques. Common parameters for ascertaining the end-of-charge condition include maximum voltage, maximum time, maximum temperature, a reduction in cell voltage with respect to time, (dV/dt,) change in temperature $\Delta T$, and increase in temperature with respect to time (dT/dt). Details of these end-of-charge indicators can be found in EDN, May 13, 1993.

Both zinc-mercuric oxide and nickel-cadmium cells suffer from additional problems such as memory effect and high self-discharge. Fast recharge often is implemented by charging the battery to some preselected voltage with a relatively high current followed by a smaller trickle charge. It is known that nickel-cadmium batteries that are fast charged cannot be charged to 100 percent of rated cell capacity. This loss of capacity is called the memory effect. Each time the battery is discharged at some low current rate, and then recharged at a higher current rate, a loss in capacity results. The capacity loss of each recharge cycle accumulates. Cells affected by the memory effect then have to be fully discharged and "reconditioned" before full capacity can be recovered. Because of this loss of capacity and high self-discharge, pacemakers with cells that suffered a memory effect had to be frequently recharged, sometimes on a weekly basis. In theory, rechargeable battery powered pacemakers were designed for a 10 year usable life. Battery chemistry problems, however, reduced the device's usable life to two or three years, the same lifetime as that of the earlier devices that employed disposable primary cells. As a result of the inherent limitations in zinc-mercuric oxide and nickel-cadmium battery cells, the assignee of the present invention has suggested the use of lithium batteries. See U.S. Pat. No. 5,411,537, issued May 2, 1995, the disclosure of which is incorporated herein by reference.

An additional problem arises with respect to recharging an implanted device's rechargeable battery. Due to the health risks and costs associated with surgical intervention, it is highly undesirable to perform surgery to access the implanted device and recharge the batteries. Some noninvasive methods for recharging implanted batteries are disclosed in the prior art. Certain patents disclose a technique for delivering electrical energy through the skin between a transcutaneous energy transfer device and an implanted medical device. For example, U.S. Pat. No. 5,350,413 discloses a transcutaneous energy transfer device comprising an external primary coil located on or near the skin, and a secondary coil for implantation under the skin. The primary and secondary coils form a transformer so that electrical current in the primary induces current in the secondary coil. An approximation to a half-wave sinusoidal voltage is developed across the primary winding by the action of a field effect transistor (FET) switching a direct current (DC) voltage source across a tuning capacitor. Because of the construction of the energy transmission device, high frequency harmonic components are present in the waveform. These high frequency components induce eddy currents in the housing of the implanted device. The temperature of the housing increases in response to the eddy currents, and can also increase in response to the elevated temperature of the battery during charging. A rise in temperature of the outer surface of the housing may be detrimental to operation of the medical device and harmful to surrounding body tissue. Industry standards suggest maximum allowable temperature rises. Limiting a temperature rise (i.e., peak temperature) is desirable to minimize the harmful effects on surrounding body tissues. Prior art systems, however, for the most part have not examined methods for reducing temperatures rises.

The prior art recharging devices suffered several drawbacks. First, many prior art systems either did not have a feature for properly aligning the external device on the patient's body over the implanted device or had such a feature but required additional circuitry (and therefore increased cost, volume, and power drain) and lacked sufficient accuracy. In addition, some prior art devices have an alignment mechanism which requires the recharging device to be turned off while alignment is measured. Also, the charging distance between the external and internal devices was limited requiring the implanted medical device to be located relatively close to the skin. Further, some systems included on implantable device consisting of two separately housed parts, an electronics unit and a receiving coil, which increased the difficulty and risk associated with surgical implantation as well as reducing the quality of the hermetic seal.

It would be desirable to provide a battery charging system that overcomes these and other problems associated with rechargeable implantable devices. In particular, it would be desirable to construct a battery charging device which can efficiently charge a battery in an implanted medical device at a relatively high power transfer rate while reducing the peak temperature generated by the device. Similarly, it would be desirable to develop an alignment mechanism that is located in the recharging device, which requires no extra components in the implanted device besides those components needed for charging. It would further be advantageous to develop an energy transmission system that minimizes the size of the receiving coil and permits the coil to be located inside the housing of the implantable device. Despite the apparent advantages of such a system, to date no such system has been developed.

SUMMARY OF THE INVENTION

The present invention overcomes the shortcomings and deficiencies of the prior art by providing a transcutaneous energy transmission system with two external solid state switches that produce a substantially sinusoidal power waveform. The solid state switches connect a regulated DC voltage across an inductor and capacitor resonant circuit. The inductor forms a primary coil of a transformer in which current is induced in a secondary coil attached to an implanted medical device. The implanted medical device receives the induced current for charging rechargeable batteries. Two different charging protocols are implemented to minimize the peak temperature produced on the outer surface of the housing of the implanted device housing or can.

Using a first charging protocol, an initial relatively high charging current is generated by an external charging device, followed by a lower charging current. The present invention includes a primary current control circuit that provides control signals to an inverter. Based upon the status of the control signals, the invention produces charging current at either a high or low level to provide efficient charging without an excessive temperature rise in the implanted device.

Charging efficiency is maximized through the use of two different resonant circuit configurations in the implanted medical device. An automatic switching mechanism is used to switch between the two resonant circuit configurations based on the magnitude of charging current. In one configuration, a capacitor connected in parallel across the secondary coil is used for relatively low levels of charging current, whereas a series connected capacitor is used for higher charging current levels. A current sensor provides an input to a switch drive that activates switches to connect one or the other of the capacitors to the charging circuit based upon the magnitude of the charging current.

In a second charging protocol, the transcutaneous energy transmission device produces a relatively high charging current to the battery, but is periodically interrupted by periods without any charging current. The resulting duty cycle of the charging current is adjustable to allow for different levels of average charging current to the battery. An effective current step is thus generated by reducing the duty cycle of the charging current from an initial high level to a lower level. The initial charging duty cycle preferably is 100% (constant DC current). Because only one relatively high charging current is produced, albeit interrupted by periods of no current, only the series connected capacitor is used and no automatic switching mechanism and parallel capacitor are necessary.

The coils of the external energy transmission device and the implanted medical device must be properly aligned for efficient energy transmission. Accordingly, an alignment circuit and indicator are provided to indicate whether the coils are properly aligned. The alignment circuit continuously senses current in the primary coil to determine whether the angular and lateral alignment is optimal by sensing a peak DC current. A visual and/or audible signal is provided only when the charging coil is substantially in alignment with the receiving coil in the implanted device thereby indicating proper alignment,

BRIEF DESCRIPTION OF THE DRAWINGS

Other objects and advantages of the invention will become apparent upon reading the following detailed description and upon reference to the accompanying drawings in which:

FIG. 8 is an electrical schematic diagram showing additional details of the inverter circuit of FIG. 5;

FIG. 9 is an electrical schematic diagram of an amplifier constructed in accordance with a preferred embodiment of FIG. 5;

FIG. 10 is an electrical schematic diagram showing the preferred peak detector circuitry of FIG. 5;

Figure 1:
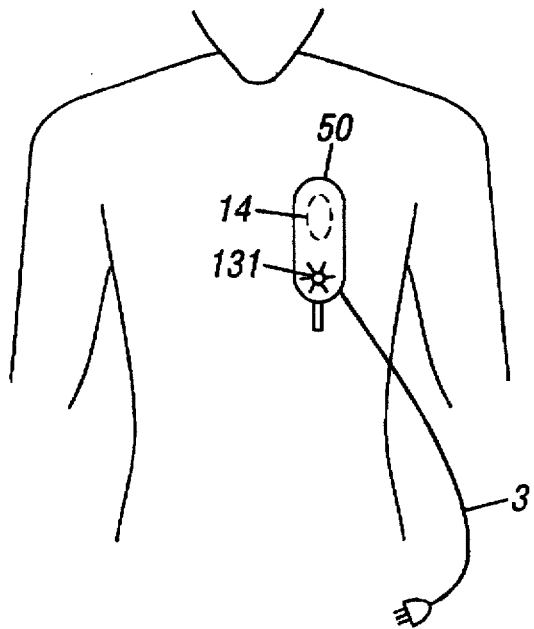
FIG. 1 is a drawing showing the external transcutaneous energy transmission device and implantable medical device of the present invention positioned to charge the batteries in the implantable device.

While the present invention is susceptible to various modifications and alternative forms, specific embodiments thereof are shown by way of example in the drawings and will herein be described in detail. It should be understood, however, that the drawings and detailed description thereof are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENT

Figure 2:
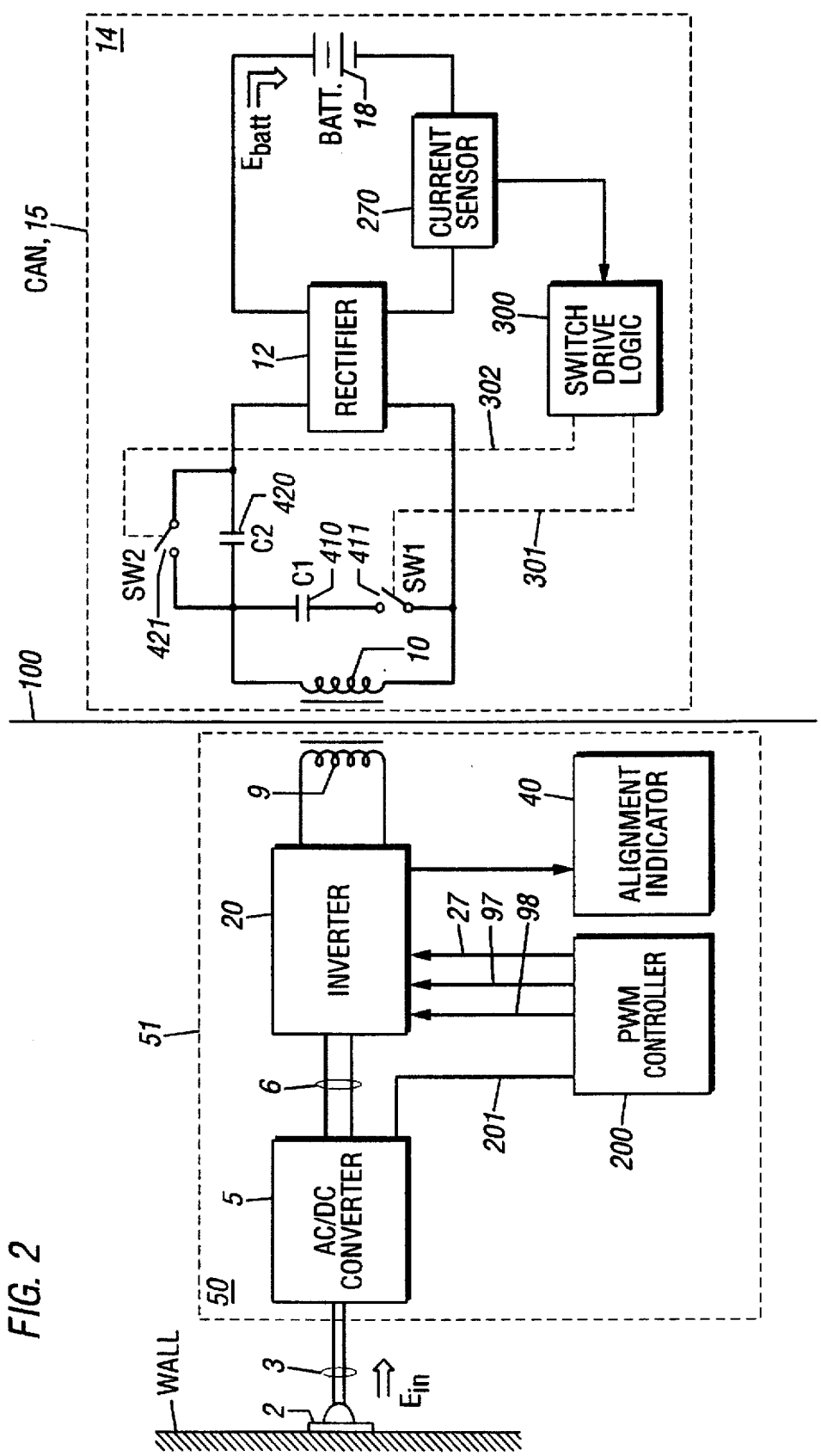
FIG. 2 is a schematic block diagram of the preferred circuit implementation of the present invention.

Referring now to FIG. 1, the transcutaneous recharging system of the present invention includes a transcutaneous energy transmission (TET) device 50 and an implanted medical device 14. In FIG. 1, the medical device 14 is shown implanted beneath the skin in the chest or pectoral region of the patient, as might be the case with a defibrillator device, with external TET device 50 positioned on, or near, the surface of the skin and placed proximally to the implanted device 14. One skilled in the art will understand, however, that the energy transmission device 50 may be used to charge any implanted medical device, wherever located. In accordance with the preferred embodiment, the implanted medical device 14 is housed in a housing or "can" made of titanium or stainless steel. Although the energy transmission device 50 is shown with a generally rectangular configuration it should be understood that the energy transmission device may take any desired shape. Power to the TET device 50 is provided via cord 3 from an external power source such as a 120 VAC outlet on batteries (FIG. 2). An indicator 131 illuminates when TET device 50 is correctly aligned with the implanted device 14 for maximum charging efficiency.

Referring now to FIG. 2, TET device 50 of the transcutaneous recharging system generally comprises a AC/DC converter 5 and an inverter 20 connecting via conductors 6. An alignment indicator 40 also connects to the inverter 20 to receive signals from inverter 20 when the TET device 50 is properly aligned with respect to the implanted medical device 14 for maximum efficiency. A pulse width modulation (PWM) controller 200 controls the output power level of inverter 20 (and thus the charging current). The PWM controller 200 can also periodically interrupt the inverter's charging current, thus producing a duty-cycled charging current. The TET device 50 components preferably are housed in a single enclosure 51. In the preferred embodiment, an alternating current (AC) voltage is provided by an external power source such as 120 VAC from a wall outlet 2. The 120 VAC source is coupled to the AC/DC converter through cord 3. The 120 VAC voltage source is converted substantially to a DC voltage by AC/DC converter which also regulates the DC voltage at a level appropriate for transcutaneous energy transmission. AC/DC convert 5 also provides operational power to PWM controller 200 over conductor 201. One of ordinary skill in the art will recognize that a multitude of known circuit implementations are possible for AC/DC converter 5, and thus the present invention should not be limited to any particular embodiment for AC/DC converter 5.

The regulated DC voltage output signal of the AC/DC converter 5 is transmitted to the inverter 20, which converts the regulated DC voltage output to a sinusoidal current that flows through primary coil 9. Electrical current in primary coil 9 electromagnetically induces a corresponding current in a secondary coil 10 which preferably is located in the implanted medical device 14. Alternatively, secondary coil 10 may be external to housing 15 of the implanted device 14, but electrically coupled to the implantable device 14. In either case, the electrical energy of primary coil 9 couples transcutaneously between primary and secondary coils through the patient's skin 100.

Referring still to FIG. 2, the implanted device 14 preferably includes a rectifier 12, battery 13 and a resonant circuit comprising secondary coil 10, parallel capacitor 410, and series capacitor 420. The resonant circuit in the implanted device 14 preferably is tuned to the frequency of the AC current in the primary coil 9. Capacitors 410 and 420 are both removable from the circuit by switches 411 and 421, respectively. A switch drive logic 300 controls the state (open or closed) of switches 411 and 421 via lines 301 and 302 depending on the amount of current through battery 13, as indicated by current sensor 270.

The rectifier 12 converts the sinusoidal voltage received by the secondary coil 10 to a DC voltage for charging the battery 13. The rechargeable battery 13 preferably comprises any of a number of different lithium chemistries, as disclosed in detail in commonly assigned U.S. Pat. No. 5,411,537, the teachings of which have been incorporated herein by reference. One of ordinary skill in the art, however, will recognize that the present invention may also be used to recharge other types of batteries, as desired.

When an alternating magnetic flux passes through a metal plate, eddy current is generated in the metal plate. The magnitude of eddy current is a function of frequency and magnitude of the magnetic flux. Eddy currents cause temperature increases. For implantable devices such as defibrillators, eddy currents are induced on the can and metal casings of components internal to the implantable device. A high charging current, therefore, creates large temperature rises. The present invention advantageously manages the level of charging current over time so as to minimize peak temperature rises without reducing the amount of charging energy delivered to the implantable device.

Figure 3:
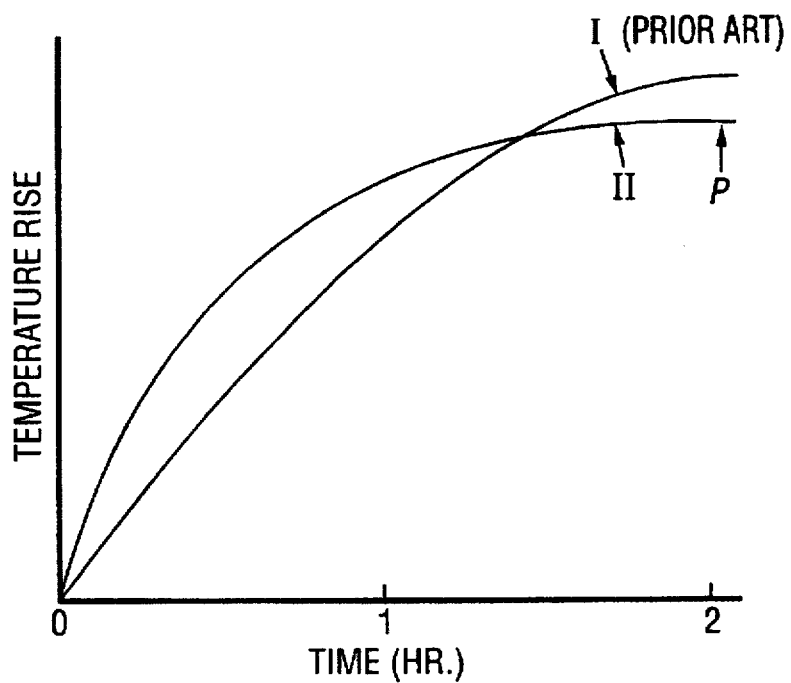
FIG. 3 is a graphical illustration depicting the temperature rise which occurs during battery charging for constant current prior art chargers relative to the charging protocols of the present invention.

For typical prior art charging systems, which often implement constant current charging protocols, the temperature rise represented by curve I in FIG. 3 is exemplary. The present invention is capable of delivering the same amount of energy to the battery in the same amount of time as prior systems, but can do so in such a manner that the peak temperature of the battery is less than it would be for prior systems. Curve II exemplifies the temperature rise response of the present invention. Significantly, the peak temperature produced by the present invention is less than the peak temperature of the prior art charging system represented by curve I, as reflected at point P.

Figure 4A:
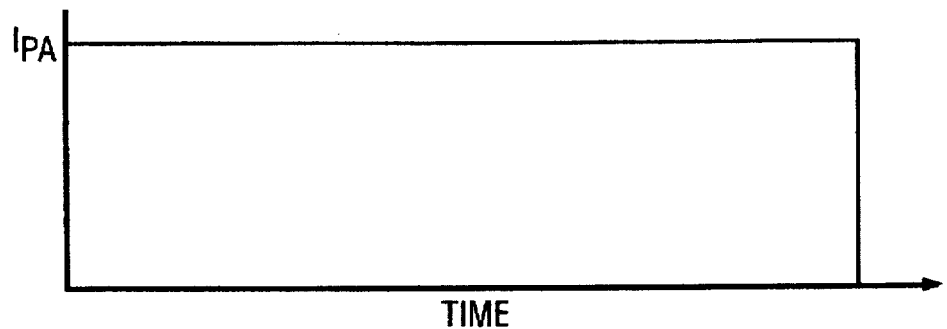
FIG. 4A shows a charging protocol for a typical prior art charging system.
Figure 4B:
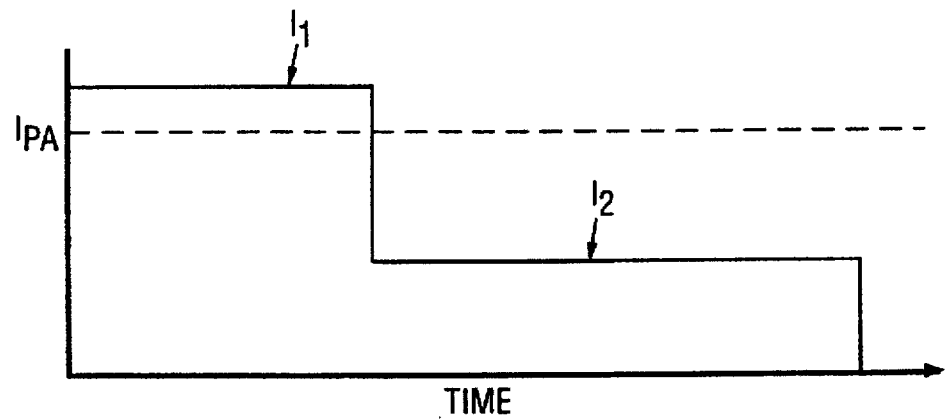
FIG. 4B shows a preferred charging protocol for use with the invention of FIG. 2.
Figure 4C:
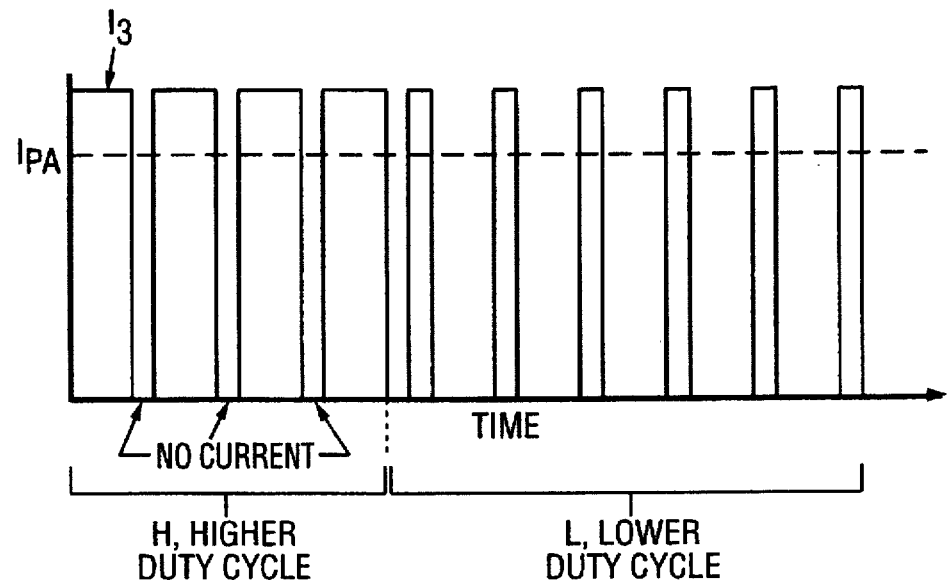
FIG. 4C shows an alternative charging protocol for use with the invention of FIG. 2.

Prior art recharging systems often charge the battery at a constant current as exemplified in FIG. 4A. As shown in FIG. 4A, a prior art constant current $I_{pA}$ is delivered to the battery for the entire charging period. To deliver the same amount of energy to the battery in the same period of time, the recharging system of the present invention preferably initially delivers to the battery a charging current 14 (which is higher than $I_{pA}$) for a first predetermined period of time, followed by a lower current $I_2$, which is lower than $I_{pA}$ for the remainder of the charge cycle as shown in FIG. 4B. The energy delivered and time required using the recharging system of the present invention embodied in the preferred protocols of FIGS. 4B and 4C are substantially the same as the energy delivery and time requirement for the prior art charging protocol of FIG. 4A. However, the peak temperature rise of the implantable device can 15 is less using the protocol of FIG. 4B, referred to in this description as the "current step" protocol.

An alternative method for achieving the same result is shown in FIG. 4C. Using this protocol, a charging current $I_3$, which is higher than $I_{pa}$, is delivered to the battery with intermittent periods with no charging current. Because of the periodic intervals without current, the effective charging current per unit time is substantially less than the peak current $I_3$. Moreover, the average current delivered to the battery is a direct function of $I_3$ and the duty cycle of the charge current waveform. The average current, therefore, is higher during the charging period in which a higher duty cycle is used as indicated in interval H in FIG. 4C. As the duty cycle is reduced during internal L, the result is a lower average charging current. The charging protocol of FIG. 4C is hereinafter referred to as the "duty cycle" charging protocol. The resulting effect of this duty cycle charging protocol is a step-down in average charging current.

Consistent with the preferred embodiment, a duty cycle of 100% may be implemented during the H interval of the charging protocol of FIG. 4C. In other words, the initial high charging current phase of the protocol of FIGS. 4C may be identical to that of FIG. 4B, but where the protocol of FIG. 4B reduces the current magnitude to $I_2$, the protocol of FIG. 4C maintains the same high current magnitude while duty cycling the current waveform to achieve a lower average charging current.

Figure 5:
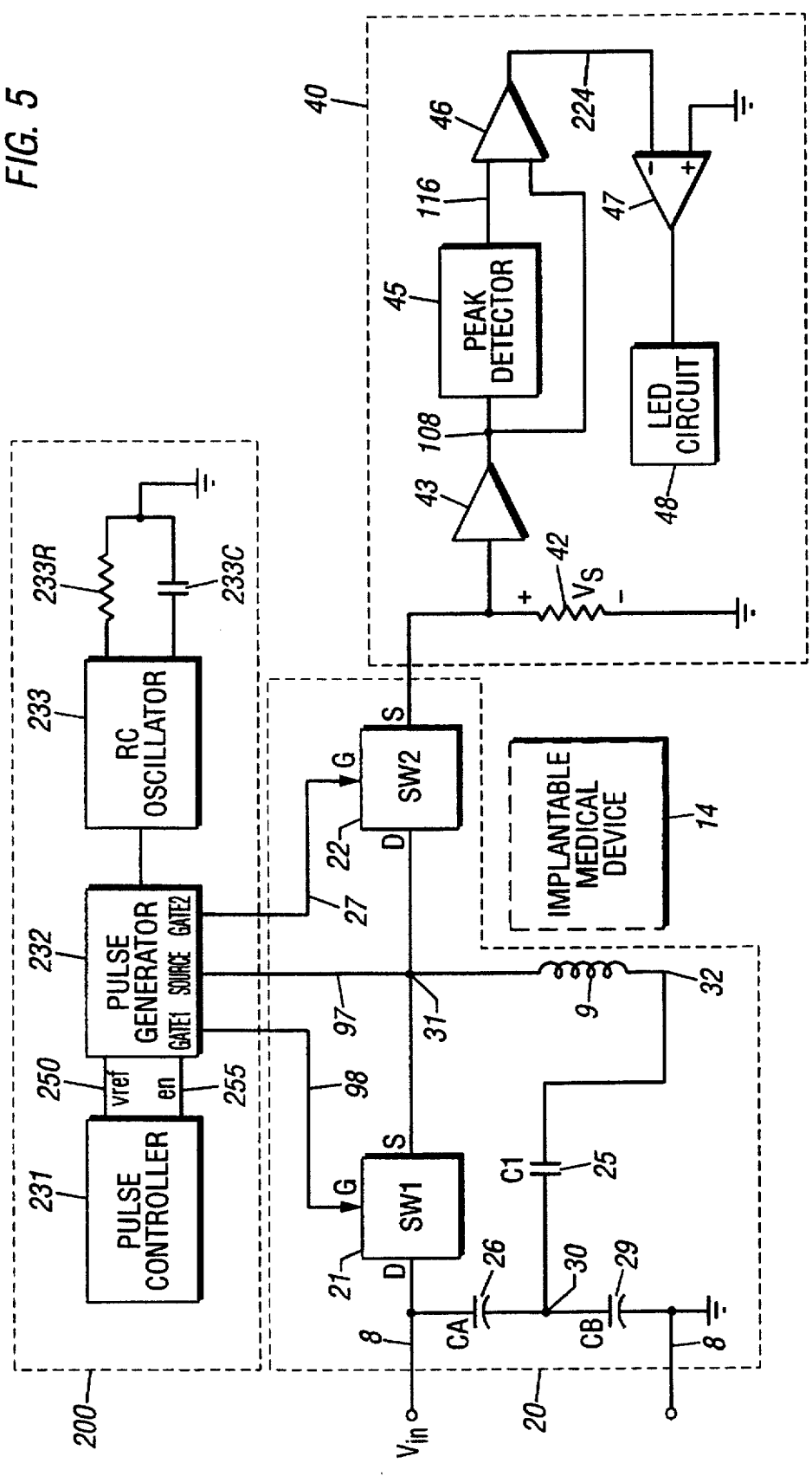
FIG. 5 is a schematic block diagram providing additional details regarding the inverter, PWM controller, and alignment indicator of the transcutaneous energy transmission device shown in FIG. 2.

FIGS. 5–8 show preferred implementations of the circuitry employed to achieve the charging protocols shown in FIGS. 4B and 4C. Referring initially to FIG. 5, the PWM controller 200, inverter 20, and alignment indicator 40 of TET 50 are shown in more detail. In accordance with the preferred embodiment, the inverter 20 includes a pair of switches 21, 22, a pair of capacitors 26, 29, and a tuning capacitor 25. The PWM controller 200 preferably includes a pulse controller 231, a pulse generator 232, an RC oscillator 233, resistor 233R, and capacitor 233C. One of ordinary skill in the art will recognize other circuit implementations are possible for PWM controller 200. The PWM controller 200 preferably includes functions such as dual output capabilities and high source and sink current.

Figure 6:
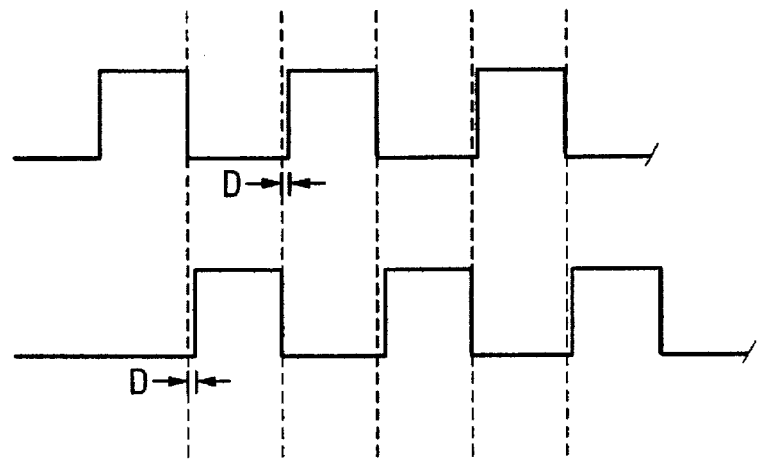
FIG. 6 is a timing diagram depicting the voltage at switches SW1 and SW2 in FIG. 5.

High frequency harmonic content in the current conducted through primary coil 9 will induce eddy currents in the housing or can 15 of the implantable medical device 14 causing a detrimental increase in can temperature. In addition to the benefits provided by employing the preferred charging protocols of FIGS. 4B and 4C, the present invention advantageously minimizes the increase in can temperature $\Delta T$ by generating a charging current signal having a substantially full sinusoidal waveform with little harmonic content. This sinusoidal charging current signal is transcutaneously transmitted to the implanted medical device 14 to charge the battery 13. To generate the desired symmetrical sinusoidal waveform, the inverter 20 includes two switches, 21 and 22 (SW1 and SW2, respectively). Preferably these switches 21, 22 are solid state devices and, as shown in FIG. 8, may be implemented with metal oxide field effect transistors (MOSFET's) 21 and 22. As shown in FIGS. 5 and 6, the output of pulse generator 232 turns switches 21 and 22 on and off alternately such that only one switch is "on" (i.e., conducting electricity) at any given time. As shown in FIG.

6, a short time period D (for example, 2 microseconds) is provided after one switch turns off and before the other switch turns on. This "dead time" between activation of switches 21, 22 insures that the switches are not on simultaneously which may cause a short circuit condition between the voltage input terminal $V_{in}$ and ground. The dead time between switching off one switch and turning on the other preferably is modified to control the charging current applied to the batteries, consistent with the current step protocol of FIG. 4B, and as described more fully below. Increasing the time when both switches 21, 22 are off results in a decrease in the power supplied to the primary charging coil 9.

Switches 21 and 22 preferably are turned on for the same amount of time each cycle to produce a symmetrical voltage waveform across junctions 30 and 31. Capacitors 26 and 29, which preferably have identical values, form a voltage divider network. Tuning capacitor 25 connects between the common connection point for capacitors 26 and 29 (junction 30) and terminal 32 of transformer 9. It should be noted that this duty cycle is not the same duty cycle described in FIG. 4C. The implementation of the duty cycle protocol of FIG. 4C is described below.

In order to minimize the eddy current induced in the housing or can 15 of implantable device 14, the operational (or carrier) frequency of the PVVM controller 200 preferably is set at 5 KHz, but it may be set to operate within a range of 1 KHz and 40 KHz. Tuning capacitor 25 is selected to generate the desired current amplitude with the primary coil 9 leakage inductance so that a sinusoidal alternating current waveform flows through the primary coil 9 with little high frequency harmonics. Through proper selection of the value of capacitor 25, the natural resonant frequency of the resonant circuit formed by primary coil 9 and capacitor 25 can be controlled to be slightly less than the operational frequency in order to achieve the zero-voltage turn-on of both switches 21 and 22.

In general, the inverter 20 produces a purely sinusoidal transfer current waveform between coils 9 and 10 using a resonant circuit comprising the leakage inductance of primary coil 9 and tuning capacitor 25. Resonance is continuously maintained by alternately activating switches 21 and 22. The present invention can provide a wide range of charging current from 0 to 1 amperes and charging voltage from 0 to 20 V. The distance between coil 9 and coil 10 preferably is less than 2.5 inches. Although a purely sinusoidal current waveform is preferred to reduce eddy currents (and thus temperature elevation) which in part are created by higher frequency harmonics, the present invention further reduces temperature rises by using the charging protocols of FIGS. 4B and 4C as described below.

Figure 7:
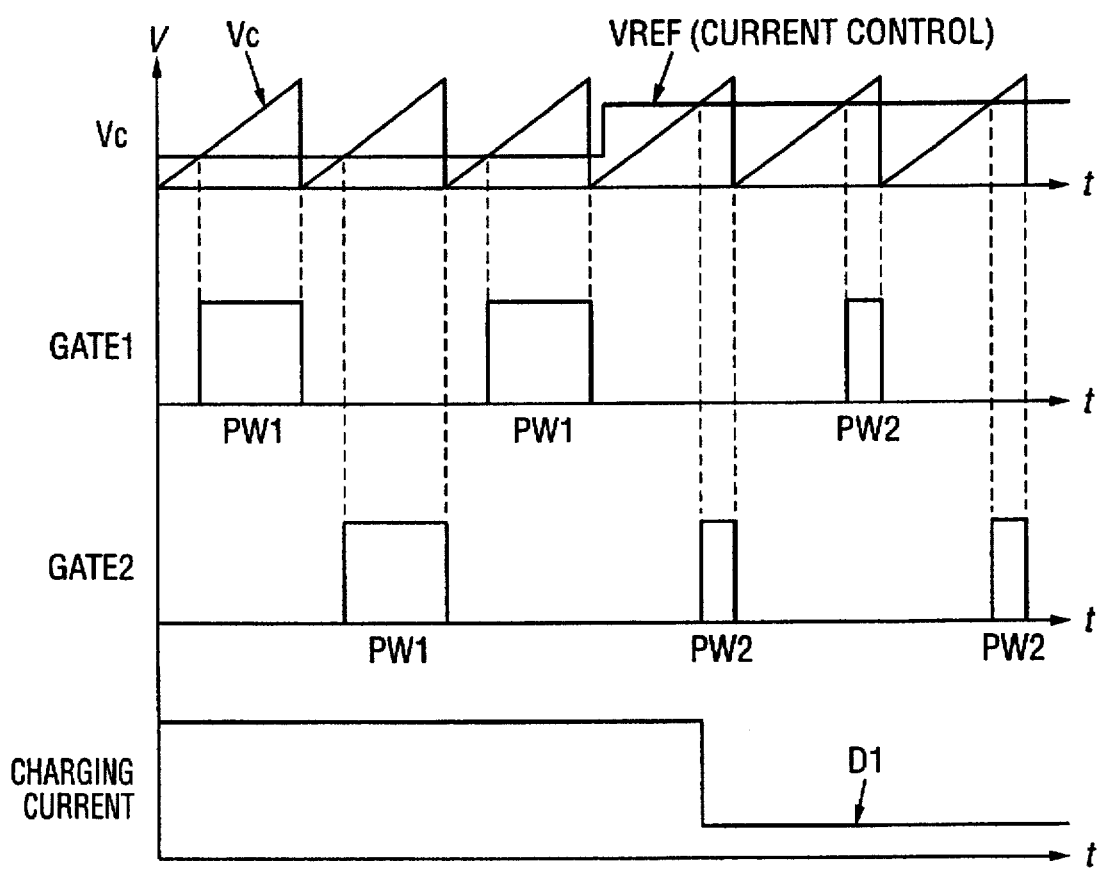
FIG. 7 is timing diagram depicting the use of a voltage reference to the PWM controller of FIG. 5 to change the magnitude of the primary coil current.

Referring now to FIGS. 5 and 7, PWM controller 200 controls the time when switches 21, 22 (SW1 and SW2, respectively) turn on, as well as the time period during which the switches are activated. Resistor 233R and capacitor 233C connect between RC oscillator 233 and ground. RC oscillator 233 provides a periodic signal. As one of ordinary skill in the art will recognize, the voltage across capacitor 233C, as indicated by $V_c$ in FIG. 5, is substantially a saw-tooth voltage waveform as shown in sub-part (a) of FIG. 7. Superimposed on the saw-tooth $V_c$ waveform is an exemplary current control signal provided by the pulse controller 231. As shown in FIG. 5, the current control signal is transmitted to the VREF input terminal of pulse generator 232 via conductor 250. FIG. 7 demonstrates how the current control signal on line 250 can be used to achieve different levels of charging current and the current step protocol of FIG. 4B. The GATE signals (GATE1 and GATE2) from the pulse generator 232 are coupled to the gate inputs G of switches 21, 22. These GATE signals dictate when each of the switches 21, 22 are turned on. Alternating cycles of the sawtooth $V_c$ waveform of FIG. 7 are used to generate the GATE signals. The first $V_c$ cycle shown in FIG. 7 produces the first GATE1 pulse in sub-part (b) of FIG. 7. The second $V_c$ cycle produces the first GATE2 pulse in sub-part (c) of FIG. 7. The third $V_c$ cycle produces the second GATE1 pulse, and so on. Each pulse is generated when the $V_c$ voltage rises above the voltage of the current control signal (VREF). The width of each GATE pulse is dictated by the point when $V_c$ rises above VP, EF and the point where $V_c$ drops below VREF, exemplified in FIG. 7 as the pulse PW1. Accordingly, by increasing the level of the current control voltage on the VREF terminal of pulse generator 232, the width of the GATE pulses are reduced as shown by pulse PW2 in FIG. 7. As described above, increasing the time when both switches 21, 22 are "off" reduces the magnitude of primary coil current, and thus charging current, as indicated in sub-part (d) of FIG. 7 at D1. Thus, the current control signal on line 250 is used by the pulse generator 232 as a reference value to vary the duty cycle of switches 21, 22 and thus control the charging current.

The pulse generator 232 preferably includes an enable input terminal (EN) which controls the status of PWM controller 200. When an enable signal is provided to the enable input via line 255, the controller is enabled. Conversely, if a disable signal appears on line 255, controller 200 is disabled. More specifically, the pulse generator 232 is enabled and disabled. According to the preferred embodiment, the enable/disable signal on line 255 is used to define a duty cycle for the current delivered to primary coil 9, according to the charging protocol of FIG. 4C.

The enable signal preferably is generated by the pulse controller 231 and transmitted via line 255 to the enable (EN) input terminal of the pulse generator 32 to turn the pulse generator on and off. Thus, for example, a logic "0" on the enable input line 255 may turn the PWM controller on, while a logic "1" turns it off. Once the pulse generator 232 is turned off through the enable signal, no current flows through the primary coil 9 and thus, the battery is not charged during the period when controller 23 is disabled. The pulse controller 231 preferably produces an enable signal similar to the duty cycle waveform of FIG. 4C. As discussed above, the resulting charging current is determined by the amplitude of the charging current when the pulse generator 232 is enabled (on) and the duty cycle of the enable input signal as one of ordinary skill in the art would understand. The amplitude of the charging current when the PWM controller 23 is on can be preset through a specified current control voltage (VREF) on line 250. Thus, the PWM controller 200 can direct the inverter 20 to produce a step down average charging current by generating an enable signal with a variable duty cycle, thereby interrupting the gate signals to switches SW1, SW2. The average charging current is directly related to the duty cycle of the enable signal. It should be noted that for the step down current protocol of FIG. 4B, the PWM controller's enable input is continuously asserted to constantly maintain the pulse generator 232 in the on condition.

Referring now to FIGS. 5 and 8, switches 21 and 22 preferably are implemented with MOSFET devices. The pulse generator 232 (FIG. 5) connects to the gate G and source S terminals of MOSFET switch 21 through conductors 98 and 97 (FIGS. 5 and 8). The source terminal S of MOSFET 21 and the drain terminal D of MOSFET 22 connect to terminal 31 of primary coil 9. The drain terminal D of MOSFET 21 connects to capacitor 26 and also receives the input regulated DC voltage $V_{in}$ on conductor 8 from AC/DC converter 5 (FIG. 2). The gate terminal G of MOSFET 22 connects to the GATE2 terminal of controller 23 via conductor 27. The source terminal S of MOSFET 22 provides a path for current from the primary coil 9 to ground through the current sensing resistor 42 of the alignment indicator 40. When switch 21 (SW1) turns on, a current path is completed from Vin, through switch 21, node 31, coil 9, capacitor 25, node 30, and capacitor 29 to ground. When switch 22 (SW2) turns on, a current path is completed from Vi., through capacitor 26, node 30, capacitor 25, coil 9, node 31, switch 22, and resistor 42 to ground. Referring now to FIG. 5, an additional advantageous feature of the present invention is an indicator for providing a visual indication of when the TET device 50 is properly positioned with respect to implanted device 14 for maximum charging efficiency. When switch 22 is turned on by controller 23, current flows from primary coil 9 through switch 22 and to resistor 42 in alignment indicator 40. Due to the symmetric AC current on the primary coil 9, the current through the switch 22 comprises half of the coil current during ne-half the time of each cycle of the AC waveform. Thus, only half of the primary coil current is received by resistor 42. In the preferred embodiment, the DC component of the voltage across the resistor 42 is used as an indication of DC input current from the voltage source $V_{in}$.

Alignment indicator 40 provides a light emitting diode (LED) in LED circuit 48 or other output device to indicate proper positioning of respect to implant with respect to implanted device 14. The TET system can be tuned so that the amplitude of the AC current through the primary coil 9 decreases when the primary coil 9 is not properly aligned with secondary coil 10. The input DC current, therefore, depends on the power draw of the load on the secondary coil and the proximity and orientation of the primary coil 9 to the secondary or receiving coil 10. Therefore, a measurement of the magnitude of the input current preferably is used in the present invention to determine if the TET device 50 is positioned properly for maximum energy transmission efficiency. The following discussion details the construction and operation of the alignment indicator 40 which uses the correlation between the input current and alignment to provide an output signal which indicates when the energy transmission device 50 is sufficiently aligned with the receiving coil 10 of the implanted device 14.

Referring to FIG. 5, the resistance value of resistor 42 preferably is small to minimize the loading effect on the inverter 20 that would otherwise result. In the preferred embodiment, resistor 42 is selected as approximately 0.5 ohms. It will be understood that the purpose of resistor 42 is to sense current in the primary coil 9 and provide an output signal indicative of the current amplitude and phase shift. Accordingly, although a resistor is preferable, any current sensing device can be used in place of resistor 42.

Referring still to FIG. 5, the alignment indicator 40 preferably includes a low-pass amplifier 43, a peak detector 45 to detect the peak DC current amplitude through switch 22, a differential amplifier 46 to amplify the difference between the peak current amplitude and the amplitude of the output current signal from low-pass amplifier 43 on line 108, a comparator 47 to compare the amplified difference with ground voltage, and an LED or other output circuit 48. In the preferred embodiment, the LED circuit 48 (or other output device) only provides an output signal indicating alignment if the present sensed current amplitude is within a predetermined range of the peak value.

Current flow through resistor 42 from switch 22 generates a voltage $V_s$ across resistor 42 which is amplified and filtered by low-pass amplifier 43 to effectively obtain the DC component of the waveform through resistor 42, and to filter out the AC portion of the waveform. The peak detector 45 senses the peak amplitude value of the output signal on conductor 108, which connects to the output terminal of the low-pass amplifier 43. The peak detector 45 stores the peak value, unless a higher amplitude is subsequently sensed. If a higher value is subsequently sensed, the peak detector 45 replaces the stored peak value with the new peak value. The output signal of the peak detector 45 on conductor 116 corresponds to the peak positive voltage sensed by the peak detector 45. This peak voltage (which is scaled to provide a threshold value that is somewhat less than the peak value), is provided as an input to the differential amplifier 46. The other input to the differential amplifier comprises the current sensed output of the low-pass amplifier 43 (conductor 108). The differential amplifier 46 amplifies the difference between the scaled peak value, and the present sensed value, and provides an output signal to comparator 47. Comparator 47 compares the difference with ground voltage, and turns on the LED circuit 48 when the current sensed value is greater than the scaled peak value. This condition will occur when the TET device 50 is positioned properly over the implanted device. In order to capture the optimum location, the primary coil 9 has to pass the optimal location at least once to let the peak detector 45 record the peak DC current value. Thereafter, the LED circuit 48 will not be turned on unless the primary coil 9 stays at the optimum location and orientation. If the lateral placement of the TET device is misaligned with respect to the receiving coil, or if the TET device 50 is positioned at a nonoptimal angle with respect to the implanted device for peak transmission efficiency, the scaled peak value will be greater than the present output voltage at the output terminals of filter 44, and the comparator 47 will produce an output signal de-activating the LED circuit 48.

One of ordinary skill in the art will recognize that a plurality of circuit implementations are possible for the low-pass amplifier 43, peak detector 45, differential amplifier 46, comparator 47, and LED circuit 48 of alignment indicator 40. In addition, the functions of two or more of these components may be performed by a single device. The circuit schematics of FIGS. 9–13 are shown as the preferred embodiment of the alignment indicator of the present invention.

As noted above, the voltage waveform across resistor 42 includes both AC and DC components. In the preferred embodiment, the AC component is filtered to permit examination of the DC component. Referring now to FIGS. 5 and 9, low-pass amplifier 43 is configured as an inverting amplifier, with an operational amplifier 103, an input resistor 102, a feedback resistor 105, a feedback capacitor 106, and an output resistor 107. The negative ratio of the resistance of feedback resistor 105 to the resistance of resistor 102 determines the DC voltage gain of the amplifier 43. Preferably, the gain is set at 100. Therefore, the resistance of resistor 105 should be one hundred times greater than that of resistor 102. Resistance values of 44.9 Kohms for resistor 105 and B449 ohms for resistor 102 are preferred, but numerous other values are possible. Capacitor 106, together with resistor 102, provide low-pass filter capabilities to amplifier 43. A resistor 104 connects the non-inverting input terminal of operational amplifier 103 to ground. The output terminal of operational amplifier 103 connects to feedback resistor 105, capacitor 106, and output resistor 107. The output of amplifier 43 (which preferably indicates a negative voltage value) is provided on conductor 108 to peak detector 45.

Referring now to FIGS. 5 and 10, the preferred construction and operation of the peak detector 45 will now be described. In the preferred embodiment, peak detector 45 comprises an operational amplifier 114, peak storage capacitor 120, and voltage follower 46. The low-pass amplifier 43 connects through conductor 108 to the non-inverting input terminal of operational amplifier 114. The output terminal of operational amplifier 114 connects to the cathode of diode 117, the anode of which connects to the cathode of diode 119. Current from operational amplifier 114 (with a negative amplitude) flows through diodes 117 and 119, charging storage capacitor 120 to a voltage indicative of the peak value at the non-inverting input of operational amplifier 114. Diode 115 prevents operational amplifier 114 from saturating in the absence of peak values, and resistor 216 provides a path through which the current from diode 115 can flow. Switch 122 resets the peak detector output signal to 0 V upon closure of that switch.

When a new peak arrives at the non-inverting input of operational amplifier 114, the output of op amp 114 swings in the negative direction, turning diode 115 off (preventing current flow through resistor 216) and turning diodes 117 and 119 on, permitting capacitor 120 to charge. As the input voltage on conductor 108 drops, the output of operational amplifier 114 swings in the positive direction, turning off diode 117 and diode 119. As a result, capacitor 120 maintains its peak voltage charge, with diode 119 and resistor 118 limiting the leakage of capacitor 120. As the output voltage continues in the positive direction, diode 115 turns on to prevent saturation of the op amp 114.

The voltage follower buffer 121 not only provides a high input impedance to minimize loading on other stages of the circuitry, but also scales down the peak detected voltage through the use of a manually adjustable potentiometer 118. Potentiometer 118 connects between the output of operational amplifier 121 and ground to provide an adjustable voltage divider in which conductor 116 carries the scaled down peak voltage to an input of differential amplifier 46. The output of operational amplifier 121 is fed back to the inverting input of amplifier 121 and is provided via conductor 115 to peak detector 45.

Figure 11:
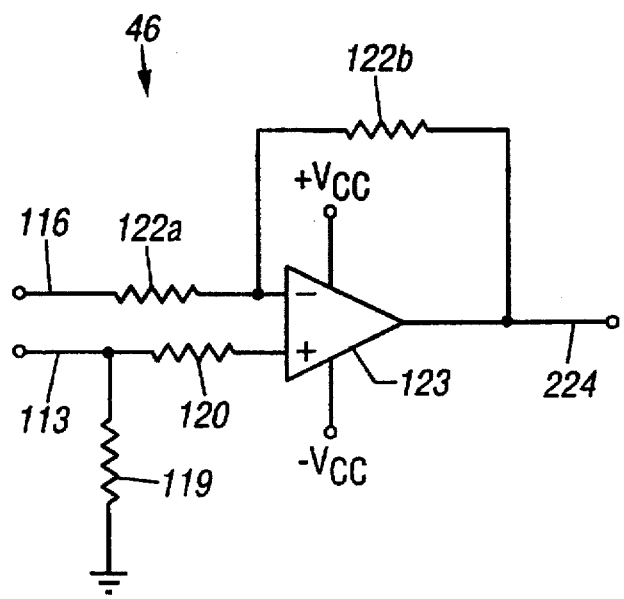
FIG. 11 is an electrical schematic diagram depicting the difference amplifier and associated circuitry of FIG. 5.

Referring now to FIG. 11, the differential amplifier 46 preferably comprises an operational amplifier 123, a feedback resistor 122b, and input resistors 120, 122a. The output signal from peak detector 45 couples to the inverting input terminal of operational amplifier 123 through resistor 122a. The output signal from the low-pass amplifier 43 couples through resistor 120 to the non-inverting input terminal of operational amplifier 123. Operational amplifier 123 amplifies the difference between the scaled peak value on conductor 116, and the present sensed value on conductor 108, and provides the amplified difference as its output 224. In the preferred embodiment of FIG. 11, the resistance of resistor 122b is equal to the resistance of resistor 119, and the resistance of resistor 122a is equal to the resistance of resistor 120, to provide a gain for difference amplifier 46 that equals the ratio of resistor 122b to resistor 122a.

Figure 12:
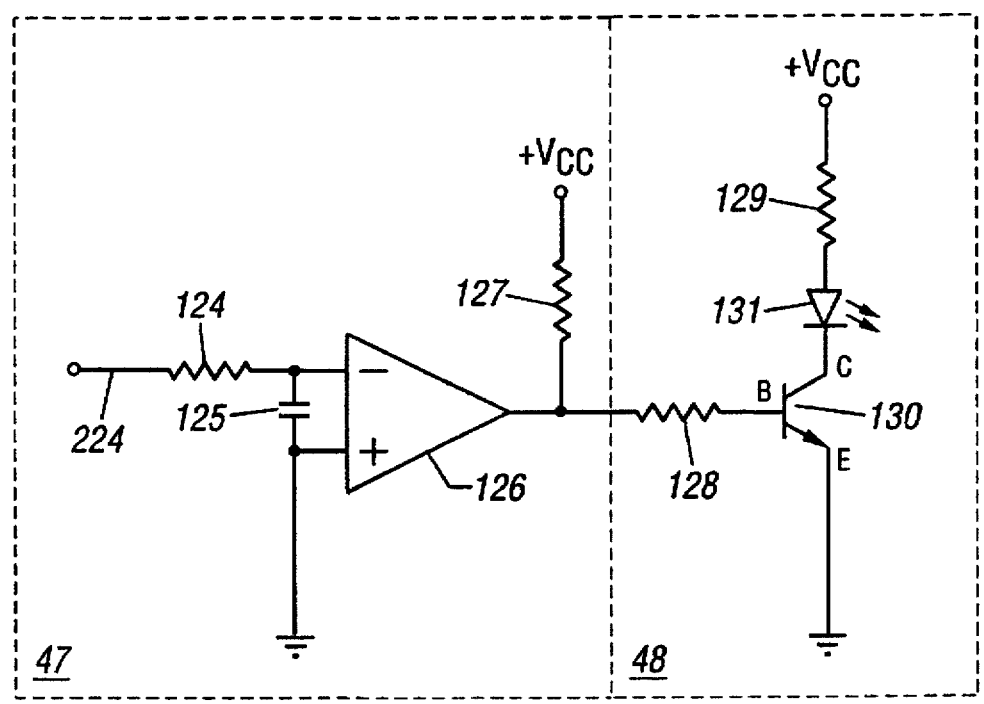
FIG. 12 is an electrical schematic diagram of the comparator and LED circuit of FIG. 5.

Referring now to FIGS. 5 and 12, the comparator 47 and LED circuit 48 are shown in detail. The comparator circuit 47 preferably comprises a comparator 126, a pull-up resistor 127, input resistor 124, and capacitor 125. The LED circuit 48 includes an LED 131, transistor 130, current limiting resistors 128 and 129. The output of differential amplifier 46 preferably connects via conductor 224 to the inverting terminal of comparator 126, through input resistor 124. The non-inverting input terminal of comparator 126 connects to ground, and to the inverting input terminal of comparator 126 through capacitor 125. The output of comparator 126 provides an input signal to the LED circuit 48 to turn on LED 131, or an alternative output device. Resistor 127 comprises a pull-up resistor which may be necessary if comparator 126 has an open-collector output stage. In the preferred embodiment, the output terminal of comparator 126 connects to the base terminal B of transistor 130 through current limiting resistor 128. Power from the voltage source +V$_{cc}$ is provided to LED 131 through resistor 129 when transistor 130 is turned on by the supply of sufficient base current from the comparator 126 to the base terminal B of the transistor 130. Although an NPN transistor is shown in FIG. 12, one of ordinary skill in the art will recognize that other types of LED driver circuits are possible, including the use of PNP transistors, and the present invention should not be construed as limited by the particular circuit embodiment shown in FIG. 12. Similarly, although an LED 131 is shown as the output device, it will also be understand that other output devices, such as audible indications, may be used as an alternative, or in addition to LED 131.

An important parameter associated with a recharging system is charging efficiency. Referring to FIG. 2, recharging efficiency can be defined as the ratio of the electrical energy input to the charging system, $E_{in}$, in TET device 50 that is to the energy delivered to the battery, $E_{batt}$, in implantable device 14. Part of the energy coupled to the implanted device that is not delivered to the battery 13 is converted to thermal energy detrimentally heating the implanted device. Thus, it is desirable to maximize recharging efficiency in order to minimize temperature increases of the implantable device.

Figure 13:
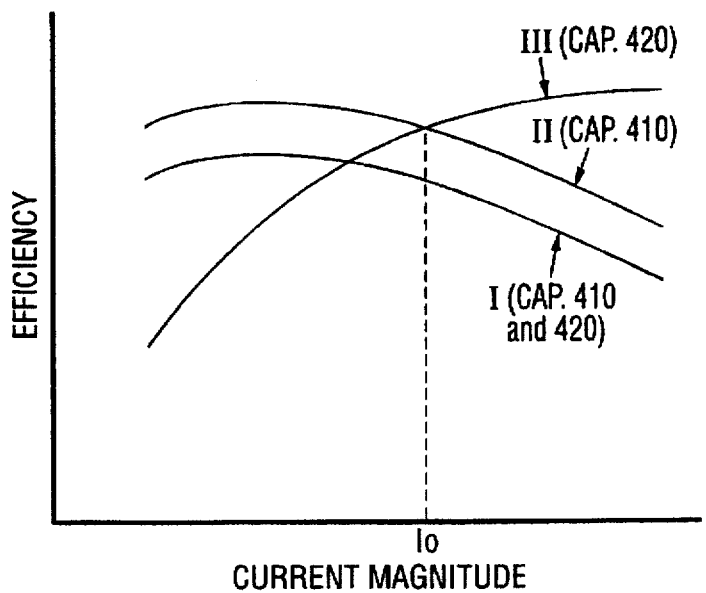
FIG. 13 shows a comparison of charging efficiency versus current magnitude for different tuning capacitor configurations.

Referring now to FIG. 13, it has been determined that charging efficiency is a function of the magnitude of the charging current. Curve I exemplifies the efficiency when both capacitors 410 and 420 of implantable device 14 in FIG. 2 are used in the charging circuit simultaneously. Improved efficiency can be achieved if either capacitor 410 or 420 is used, but not both simultaneously. As shown in curve II, higher efficiency can be achieved using just capacitor 410 than using both capacitors together, but the efficiency still drops off at higher charging current levels. If just capacitor 420 is used (curve III), higher efficiency is obtained at higher current levels, but lower efficiency at lower current levels than if just capacitor 410 is used. To maximize charging efficiency, therefore, it is preferable to use only capacitor 410 when charging at lower current levels and only capacitor 420 when charging at higher current levels, but not both capacitors simultaneously. Current level $I_o$ may be defined as the charging current above which capacitor 420 is used and below which capacitor 410 is used.

It should be noted that the secondary circuit in implantable device 14 can be properly tuned to the frequency of the AC current through the primary coil 9 by using either capacitor 410 or 420 in conjunction with secondary coil 10. That is, battery charging is possible regardless of which capacitor is included in the preferred embodiment. However, to achieve maximum efficiency, capacitor 410 preferably is used for low current charging and capacitor 420 is used for high current charging. Accordingly, a mechanism for switching the capacitors into the circuitry is described below.

Figure 14:
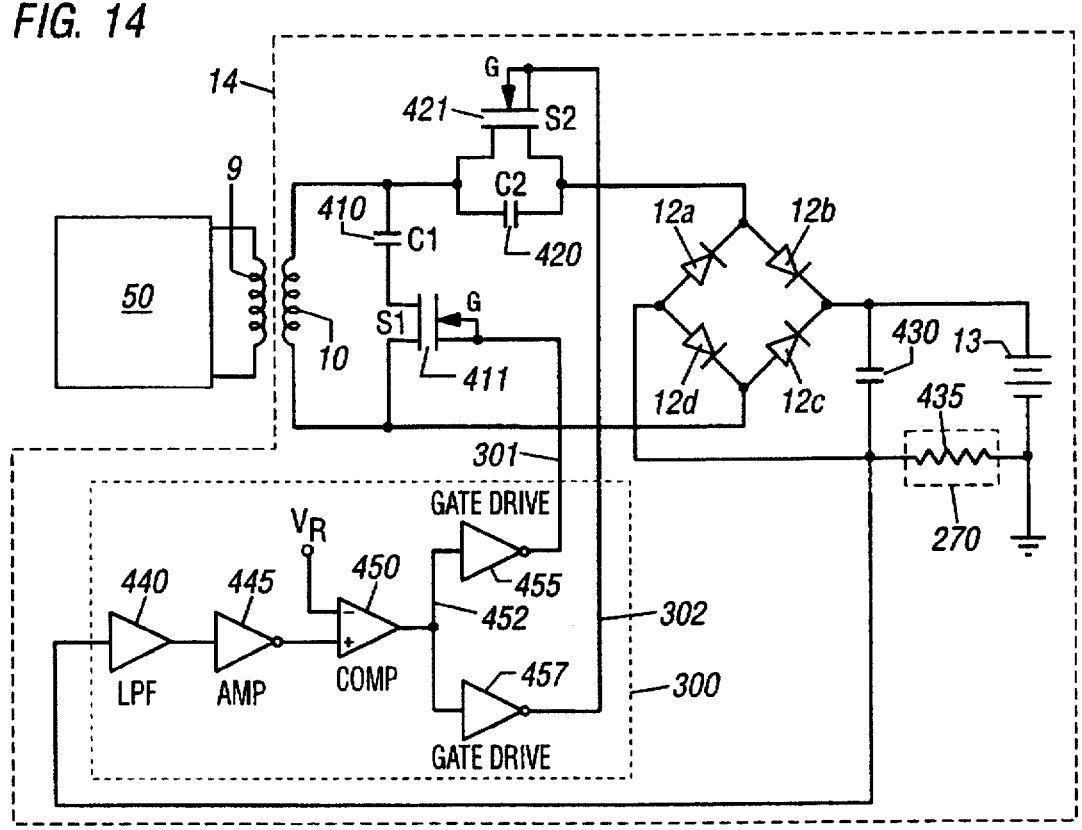
FIG. 14 is an electrical schematic of for the implantable device in charging circuitry accordance with the preferred embodiment.

Referring now to FIG. 14, switches 411 and 421 of implantable device 14 are shown consistent with the preferred embodiment as MOSFET devices. Switch 421 effectively provides a short circuit across capacitor 420 when switch 421 is closed and an open circuit when the switch is opened. Thus, opening switch 421 causes capacitor 420 to be used, which is preferable during high current charging periods (i.e., for generating current $I_1$ in FIG. 4B). Similarly, switch 411 can be opened, removing capacitor 410 from the charging circuit during high current charging. When switch 411 is closed, capacitor 410 forms part of the charging circuit, which is preferable during low current charging (for generating current $I_2$ in FIG. 4B). Preferably, switches 411 and 421 are opened for the duty cycle protocol of FIG. 4C because only a single current level is generated.

Referring to FIG. 14, the current sensor 270 (FIG. 2) preferably comprises a current sensing resistor 435. As one of ordinary skill in the art will recognize, current sensing components typically include low resistance resistors, such as 0.5 Ω resistors or less. Because one side of current sensing resistor 435 is grounded, the voltage on the other side at point S1 is proportional to the current through the resistor. Because the current sensing resistor is connected in series with the battery 13, the voltage at point S1 is proportional to the charging current applied to the battery.

Referring again to FIG. 14, the voltage at point S1 (i.e., battery current) is provided as an input to switch drive logic 300. After filtering voltage S1 to remove high frequency noise, including ringing and carrier frequency, by low pass filter 440, the filtered signal is then amplified by inverting amplifier 445. Comparator 450 compares the amplified battery current signal to a reference voltage, $V_R$, which is provided on line 447. The reference voltage $V_R$ can be generated in several ways consistent with the preferred embodiment. For example, voltage $V_R$ may be derived from the battery 13 through a voltage regulator. Reference voltage $V_R$ is predetermined so as to represent the charging current level at which it is desired to switch from capacitor 410 to 420, or vice versa. Preferably, $V_R$ is set to correspond to current level $I_o$ from FIG. 13. One of ordinary skill in the art will also recognize the benefit in incorporating hysteresis into the comparator circuit 450 to prevent the comparator from oscillating if the amplified current signal S1 hovers around the value of the reference voltage $V_R$. Low-pass filter 440, inverting amplifier 4 comparator 450 can be provided by any of a number of conventional devices, and the present invention is not limited to any specific circuit implementation.

Referring still to FIG. 14, when the amplified current signal provided to the positive terminal of the comparator 450 is greater than the reference voltage $V_R$, the output of the comparator on line 452 will become a logic high level. This high logic signal on line 452 in turn drives switches 411 and 421 open through inverting gate drives 455 and 457 which are of a type known to those of ordinary skill in the art. The low output signal of gate driver 455 on line 301 is provided to the gate terminal G of switch 411, thereby opening switch 411, and thus removing capacitor 410 from the circuit. Further, the low output signal of gate driver 457 on line 302 is provided to the gate terminal G of switch 421, thereby opening switch 421, and placing capacitor 420 in the charging circuit. Therefore, for high charging currents over the trip point set by voltage $V_R$ ($I_o$), charging efficiency is maximized by using only capacitor 420, not capacitor 410, in the charging circuit.

When charging the battery at a low current level (less than the trip point defined by $V_R$), the output signal on line 452 from the comparator 450 is driven to a low logic level because $V_R$ exceeds the output signal from inverting amplifier 445. The low logic level from the output of comparator 450 activates the inverting gate drives 455 and 457 to high output levels. A high output signal on line 301 from gate drive 455 closes switch 411 thereby placing capacitor 410 into the charging circuit. A high output signal on line 302 from gate drive 457 closes switch 421 and effectively removes capacitor 420 from the charging circuit. Therefore, for low charging currents (less than the trip point set by voltage $V_R$), charging efficiency is maximized by using only capacitor 410, not capacitor 420, in the charging circuit.

Finally, referring to FIGS. 2 and 14, rectifier 12 preferably comprises a full-wave bridge rectifier including diodes 12a, 12b, 12c, and 12d. Capacitor 430 is provided as an output filter so that a good approximation to a DC level current is provided to battery 13.

While a preferred embodiment of the present invention has been described, one skilled in the art will understand that many modifications can be made to the present invention without departing from its principles. The following claims should not be construed as limited to the preferred embodiment described above, but instead should be construed broadly to cover all modifications and equivalents, which will be apparent to one skilled in the art.

What is claimed is:

1. A transcutaneous energy transmission system for transmitting electrical energy from an external charging device to an implantable medical device for providing power to said implantable medical device to charge a battery in said implantable medical device, said transcutaneous energy transfer system comprising:

an external charging device containing:

a primary coil in said external charger for transmitting said power transcutaneously to said medical implantable device;

a capacitor in said external charger coupled to said primary coil, said primary coil and said capacitor forming a resonant circuit;

a controller for controlling the power provided to said resonant circuit;

an implantable medical device containing:

a secondary coil in said implantable medical device;

a first capacitor connected in series to a first switch, the combination of the first capacitor and first switch connected in parallel across said secondary coil;

a second capacitor connected to said secondary coil;

a second switch connected in parallel across said second capacitor, and a battery wherein the battery connects to said second capacitor and said second switch.

2. The system of claim 1, wherein the implantable medical device further comprises a current sensor for sensing the magnitude of current charging the battery.

3. The system of claim 2, wherein the implantable medical device further comprises a switch drive for turning said first switch and said second switch on and off depending on the magnitude of current charging the battery, and wherein the magnitude of current charging the battery is indicated to the switch drive by the current sensor.

4. The system of claim 3, wherein said first switch is closed to allow current to flow through said first capacitor and said second switch is closed to short circuit said second capacitor, when a relatively low charging current is applied to said battery.

5. The system of claim 3, wherein said first switch is opened to prevent current from flowing through said first capacitor and said second switch is opened to allow current to flow through said second capacitor, when a relatively high charging current is applied to said battery.

* * * * *